(12) United States Patent
Ward

(10) Patent No.: US 8,512,350 B2
(45) Date of Patent: Aug. 20, 2013

(54) SINGLE OPERATOR MEDICAL DEVICE HANDLES AND RELATED METHODS OF USE

(75) Inventor: Tim E. Ward, Springville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1036 days.

(21) Appl. No.: 10/999,914

(22) Filed: Dec. 1, 2004

(65) Prior Publication Data
US 2006/0116692 A1 Jun. 1, 2006

(51) Int. Cl.
*A61B 17/22* (2006.01)

(52) U.S. Cl.
USPC ............................. 606/110; 606/113; 600/131

(58) Field of Classification Search
USPC ................. 606/127, 110, 113, 114, 128, 200; 600/131
See application file for complete search history.

(56) References Cited

U.S. PATENT DOCUMENTS

| 4,261,358 | A | * | 4/1981 | Vargas et al. | 604/136 |
|---|---|---|---|---|---|
| 4,345,599 | A | * | 8/1982 | McCarrell | 606/113 |
| 5,146,810 | A | * | 9/1992 | Mueller | 74/558 |
| 5,397,332 | A | * | 3/1995 | Kammerer et al. | 606/151 |
| 5,439,468 | A | * | 8/1995 | Schulze et al. | 606/143 |
| 5,470,007 | A | * | 11/1995 | Plyley et al. | 227/175.1 |
| 5,830,152 | A | * | 11/1998 | Tao | 600/562 |
| 6,217,587 | B1 | | 4/2001 | Tsuruta | |
| 6,676,668 | B2 | * | 1/2004 | Mercereau et al. | 606/127 |
| 7,094,202 | B2 | * | 8/2006 | Nobis et al. | 600/131 |
| 2003/0120281 | A1 | * | 6/2003 | Bates et al. | 606/114 |
| 2005/0070885 | A1 | * | 3/2005 | Nobis et al. | 606/1 |

FOREIGN PATENT DOCUMENTS

DE 24 28 319 A1 1/1976

OTHER PUBLICATIONS

Annex to form PCT/ISA/206—Communication Relating to the Results of the Partial International Search in PCT/US2005/043204 (2 pages).

* cited by examiner

*Primary Examiner* — Kathleen Holwerda
(74) *Attorney, Agent, or Firm* — Bookoff McAndrews, PLLC

(57) ABSTRACT

The invention is directed to improved handles for medical devices. Embodiments of the invention include handles that allow for the device's introduction, positioning, and actuation with a single hand of an operator, handles that allow an operator to simultaneously position and manipulate two devices relative to each other as well as relative to an additional medical device, such as an endoscope, and handles that allow an operator to simultaneously manipulate an endoscope and an additional medical device without the help of an assistant.

17 Claims, 12 Drawing Sheets

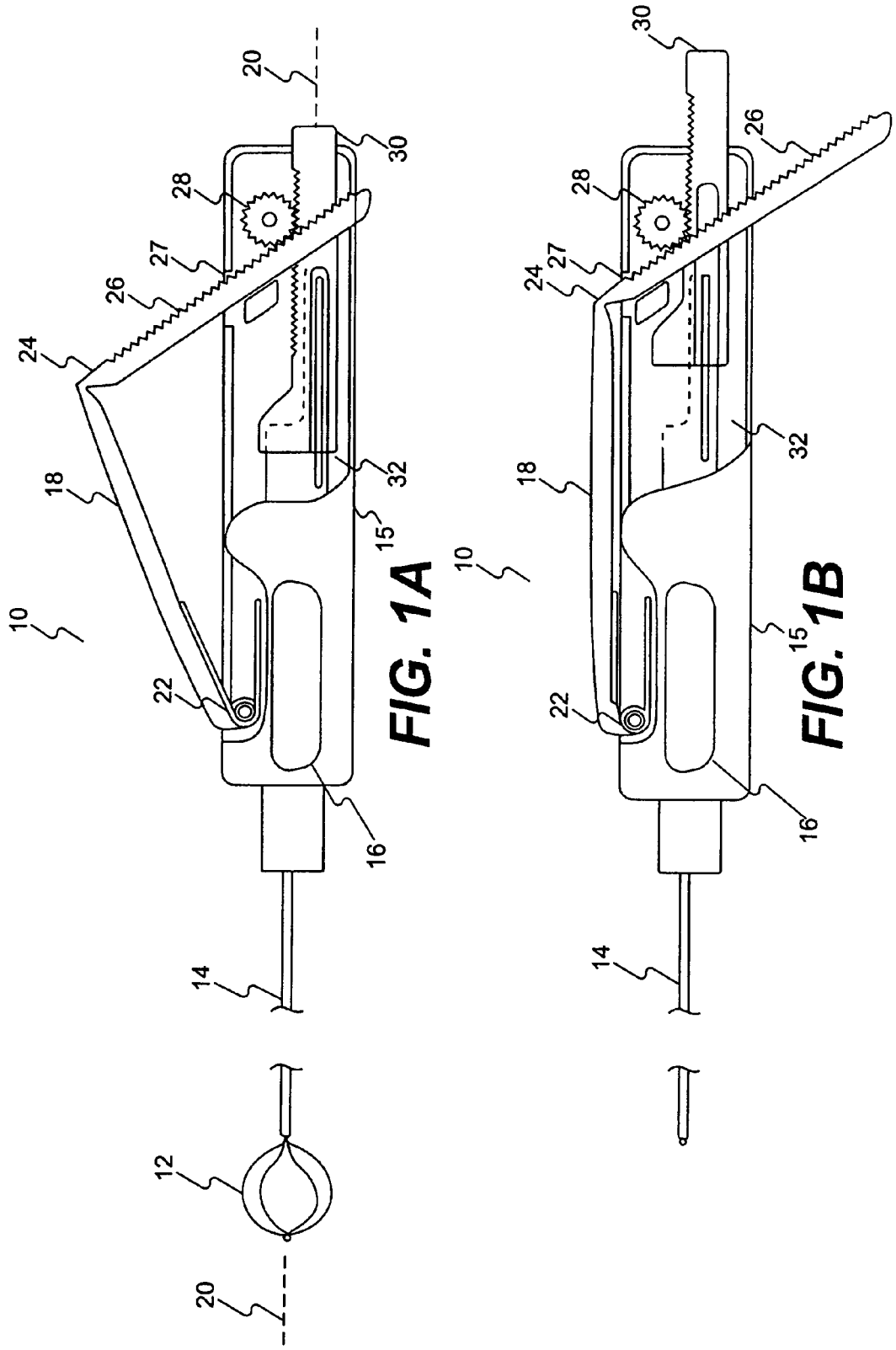

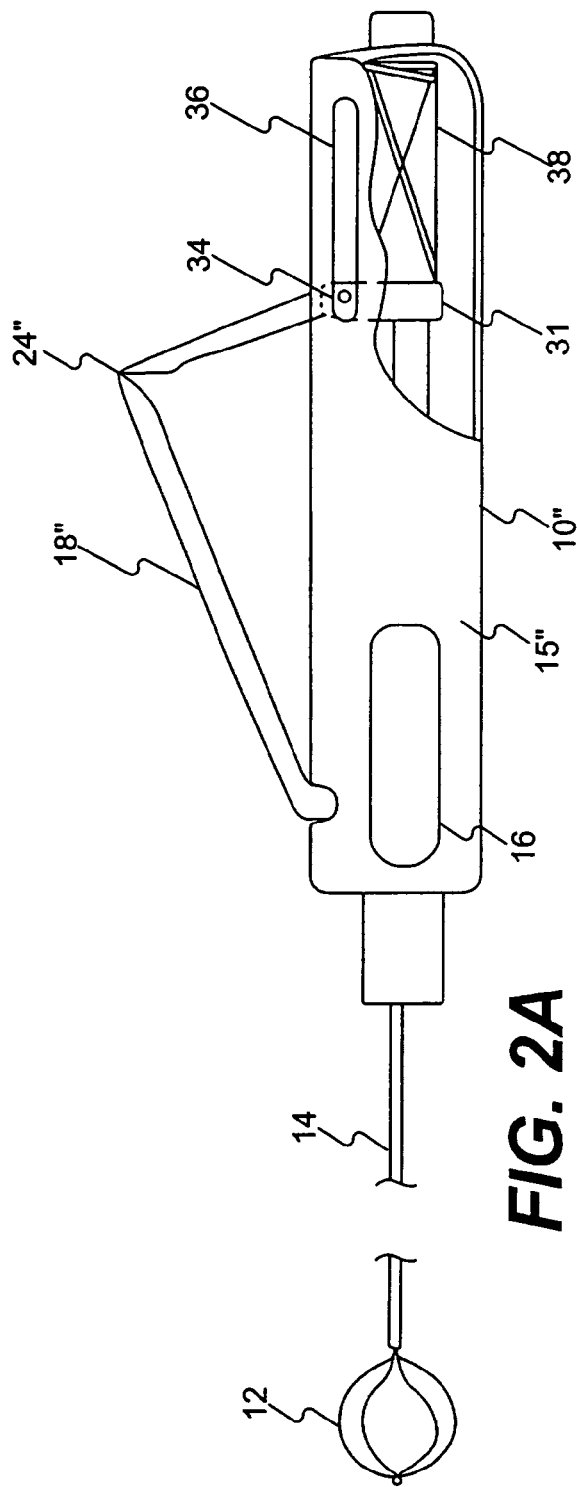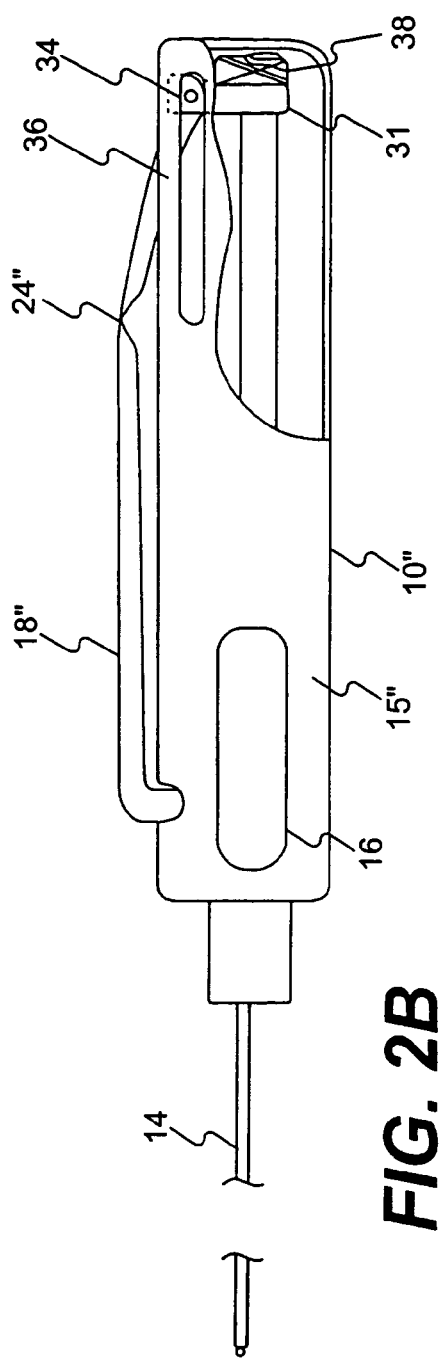
FIG. 2A
FIG. 2B

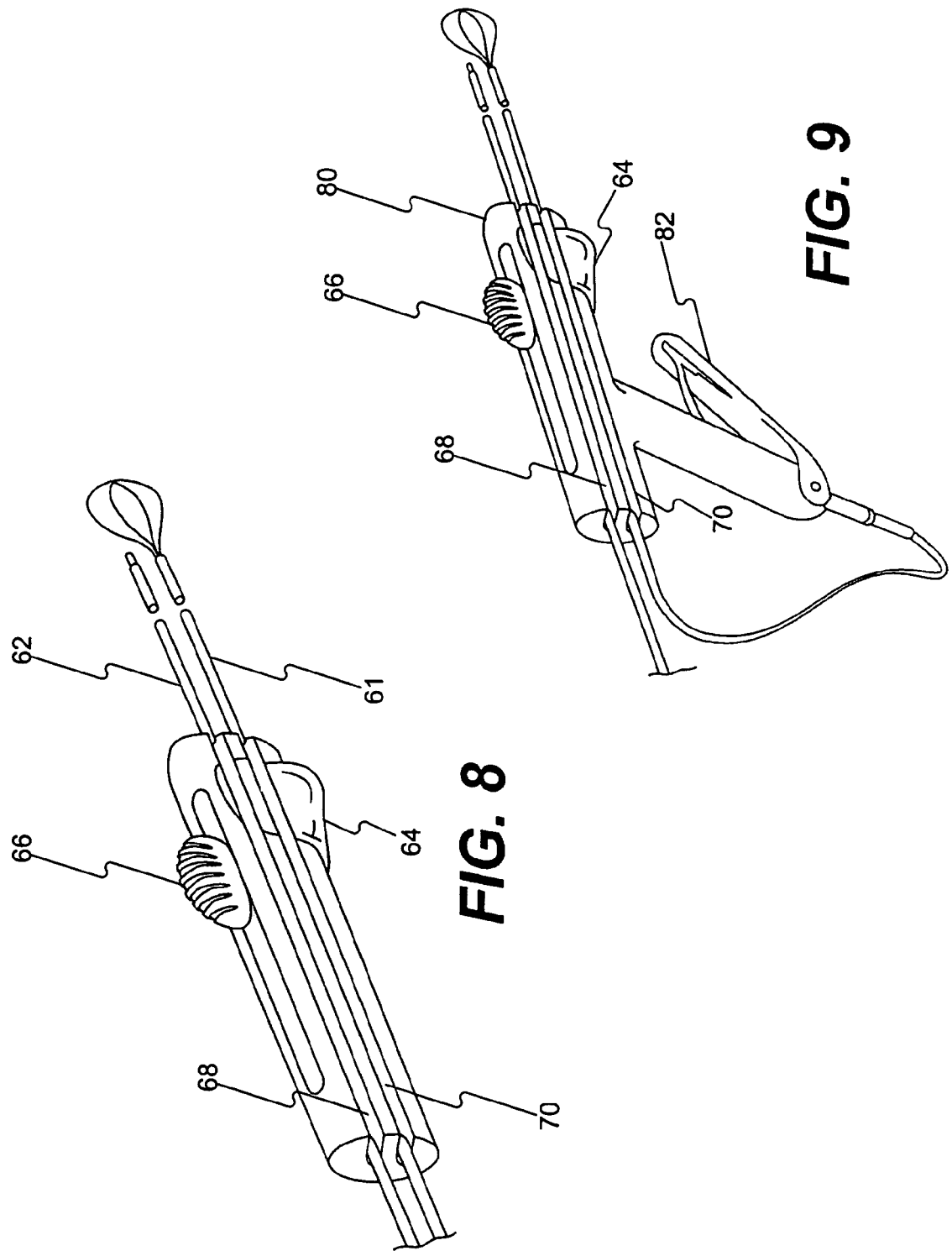

SINGLE OPERATOR MEDICAL DEVICE HANDLES AND RELATED METHODS OF USE

DESCRIPTION OF THE INVENTION

1. Field of the Invention

This invention relates to handle assemblies for medical devices and related methods of use. More particularly, embodiments of the invention relate to improved handles for actuating and positioning medical implements by a single operator including, for example, positioning multiple medical implements relative to each other during a medical procedure.

2. Background of the Invention

Medical devices having elongated body portions can be introduced through a body opening, cavity, or tract and manipulated to remove material from within the body. Such medical devices can be positioned at a treatment site through an elongated endoscope or a laparoscope, which allows an operator to simultaneously view and operate at a remote surgical site. In the field of urology, medical retrieval devices, such as collapsible baskets, graspers and the like, are used to retrieve various foreign or biological materials (e.g., kidney stones, urinary calculi, choleliths, etc.) from within a body. In certain urological procedures, a retrieval device is used to immobilize kidney stones relative to a laser fiber, which is used to fragment stones into smaller pieces for retrieval and removal by the retrieval device, for example.

Medical retrieval devices can include a sheath and an object-engaging unit, such as a basket, that is moveable relative to the sheath from a collapsed state within the sheath to another state in which the unit extends past the distal end of the sheath. The sheath typically extends from a handle, located at the proximal end (i.e., the end away from the patient) of the sheath to the object-engaging unit which is located at the distal end of the sheath (i.e., the end near the patient and that goes into the patient). The handle includes a mechanism for actuating the object-engaging unit in order to move the object-engaging unit between collapsed and extended, expanded states.

During a urological procedure, a physician needs to be able to move the distal end of the medical retrieval device in relation to the distal end of a ureteroscope. This may be accomplished by the physician gripping the sheath just proximal to the point where the retriever sheath is introduced into an auxiliary channel within the ureteroscope. As the physician operates the ureteroscope and positions the sheath of the retrieval device, an assistant actuates the handle at the physician's direction to retrieve foreign material.

In procedures that utilize a laser fiber and retrieval device, the physician must carefully hold and reposition both items relative to each other as well as relative to the ureteroscope. Currently, an operator must manipulate and actuate each device individually or with the assistance of another operator. Such procedures can become overly time consuming and cumbersome.

In light of the foregoing, there is a need for an improved handle for a medical retrieval device that allows for the device's introduction, positioning, and actuation with a single hand of an operator. There is also a need for an improved handle that allows an operator to simultaneously position and manipulate two devices relative to each other as well as relative to an endoscope. In addition, there is a need for an improved handle that allows an operator to simultaneously manipulate an endoscope and manipulate an additional medical device without the help of an assistant.

SUMMARY OF THE INVENTION

Accordingly, the present invention is directed to improved handles for a medical device, and related methods of use that obviate one or more of the limitations and disadvantages of the prior art medical device handles.

One embodiment of the invention is directed to a medical device including a sheath having a lumen, a distal end, and a proximal end. The device further includes an end effector unit and an elongate member connected to the end effector unit and extending proximally from the end effector unit within the lumen of the sheath. The end effector unit and sheath are movable relative to each other to achieve a first state of the end effector unit when the end effector unit is within the lumen of the sheath and a second state when the end effector unit extends from the distal end of the sheath. A handle is connected to the proximal end of the sheath and a proximal end of the elongate member. The handle comprises an actuating lever to selectively actuate the end effector unit between the first and second states. The handle is configured to allow a single hand of an operator to simultaneously be positioned to actuate the end effector unit via the actuating lever and grasp and manipulate the sheath.

In various embodiments, the medical device may include one or more of the following additional features: an end effector unit comprising a basket having a plurality of legs where the basket is collapsed in the first state and expanded in the second state; the elongate member is a wire connected to a proximal end of the end effector unit; the actuating lever includes a first portion connected to the handle and a second portion formed at an angle to the first portion; upon actuation, the second portion of the actuating lever engages and moves an internal portion of the handle for movement of the end effector unit between the first and second states; the actuating lever includes a first end connected to the handle and a midportion resiliently bowed away from the handle; a ring disposed along an exterior surface of the handle and positioned to accommodate a first finger of an operator's hand; the ring is disposed along an exterior surface of the handle about 90° relative to the actuating lever; and the ring is positioned relative to the actuating lever to permit a second finger of the operator's hand to actuate the actuating lever when the first finger is within the ring; where the ring is positioned relative to the actuating lever to permit a third finger of the operator's hand to grasp and manipulate the sheath when the first finger in within the ring and the second finger actuates the actuating lever.

Another embodiment of the invention is directed to a method for operating a medical device to perform an operation in a body. The method includes providing a medical device including a sheath including a lumen, a distal end, and a proximal end. The device further includes an end effector unit and an elongate member connected to the end effector unit and extending proximally from the end effector unit within the lumen of the sheath. The end effector unit and sheath are movable relative to each other to achieve a first state of the end effector unit when the end effector unit is within the lumen of the sheath and a second state when the end effector unit extends from the distal end of the sheath. A handle is connected to the proximal end of the sheath and includes an actuating lever. The method further comprises grasping the handle with a hand of an operator in a position to activate the lever; grasping the sheath with the hand grasping the handle; advancing the sheath with the hand grasping the handle to position the end effector unit near a treatment site;

and actuating the actuating lever of the handle to selectively actuate the end effector unit between the first and second states.

In various embodiments, the method may include one or more of the following additional features: manipulating material with the end effector unit at the treatment site; providing an end effector unit comprising a basket having a plurality of legs; a ring disposed along an exterior surface of the handle and, upon grasping the handle, the operator grasps the handle with a single hand and positions a first finger of the single hand within the ring; the operator grasps the handle and positions a second finger of the single hand for actuation of the actuating lever; the operator grasps the sheath with at least a third finger of the single hand in combination with another finger to grasp and manipulate the sheath; and the ring is disposed along an exterior surface of the handle about 90° relative to the actuating lever.

Another embodiment of the invention is directed to a medical device comprising an elongated handle body defining a longitudinal axis and first and second ports extending along a side of the handle body. The first and second ports are configured to receive first and second elongated medical devices respectively. A movable internal grip is movable along the longitudinal axis of the handle body and the movable internal grip is disposed within the first port. The first port is configured to receive the first elongate medical device and move the first elongated medical device relative to the handle body. A stationary internal grip is disposed within the second port and is configured to receive the second elongated medical device and hold the second elongated medical device stationary relative to the handle body.

In various embodiments, the medical device may include one or more of the following additional features: the first elongated medical device is a lithotriptor and the second elongated medical device is a tissue retrieval device; the first and second ports are recesses defined by the handle body and accessible along an external surface of the handle body; a finger slide disposed external to the handle body and connected to the movable internal grip; a biasing member inside the handle body between the movable internal grip and a forward end of the handle body for providing resistance to forward movement of the movable internal grip; multiple stationary internal grips disposed within the second recess port; an actuating mechanism to actuate an end effector unit of the second elongated medical device; and the actuating mechanism extends from the handle body in a direction perpendicular to the longitudinal axis of the handle body.

In another embodiment, the invention is directed to a method for performing an operation in a body, comprising providing a handle including an elongated handle body defining a longitudinal axis and first and second ports extending along a side of the handle body. The handle includes a movable internal grip movable along the longitudinal axis of the handle body and disposed within the first recess port. A stationary internal grip is disposed within the second port. The method further comprises inserting a first medical device within the first port and engaging the first medical device with the movable internal grip; inserting a second medical device within the second port and engaging the second medical device with the stationary internal grip; and moving the first medical device relative to the handle body and the second medical device by longitudinal movement of the movable internal grip.

In various embodiments, the method may include one or more of the following additional features: positioning the first and second medical devices at a treatment site relative to a distal end of an endoscope; inserting the first and second medical devices into a channel of the endoscope; the first medical device is a lithotriptor and the second elongated medical device is a tissue retrieval device; providing a biasing member inside the handle body between the movable internal grip and a forward end of the handle body for providing resistance to forward movement of the movable internal grip; providing an actuating mechanism to actuate an end effector unit of the second medical device; and providing the actuating mechanism to extend from the handle body in a direction perpendicular to the longitudinal axis of the handle body.

In another embodiment, the invention is directed to a medical device, comprising a sheath including a lumen, a distal end, and a proximal end, an end effector unit and an elongate member connected to the end effector unit and extending proximally from the end effector unit within the lumen of the sheath, the end effector unit and sheath movable relative to each other to achieve a first state of the end effector unit when the end effector unit is within the lumen of the sheath and a second state of the end effector unit when the end effector unit extends from the distal end of the sheath. The medical device further includes a handle connected to the proximal end of the sheath and a proximal end of the elongate member. The handle comprises an actuator to selectively actuate the end effector unit between the first and second states, wherein the handle is configured for releasable engagement with an endoscope.

In various embodiments, the medical device may include one or more of the following additional features: a device port defining an internal lumen extending through the handle along a longitudinal axis; wherein the actuator extends along an axis transverse to the longitudinal axis of the internal lumen; wherein upon engagement of the handle with an endoscope, the internal lumen of the device port communicates with an internal lumen of the endoscope; wherein movement of the actuator along the axis transverse to the longitudinal axis of the internal lumen actuates the end effector unit between the first and second states; wherein the actuator includes a plunger; wherein a spring biases the actuator toward a position corresponding to the first state of the end effector unit; wherein the sheath is within the internal lumen of the device port and beyond a distal end of the handle; a second device port defining a second internal lumen extending through the handle along a second longitudinal axis substantially parallel to the longitudinal axis of the internal lumen; a lithotriptor within the second internal lumen of the second device port beyond a distal end of the handle; wherein the handle includes a connector configured for threaded, snap fit, or a male/female connection engagement with an endoscope.

In another embodiment, the invention is directed to a method for operating a medical device to perform an operation in a body comprising, providing a medical device comprising, a sheath including a lumen, a distal end, and a proximal end, an end effector unit within the lumen of and movable relative to the sheath, a handle connected to the proximal end of the sheath, the handle including an actuator to actuate the end effector unit. The device includes a device port defining an internal lumen extending through the handle and a connector configured for releasable engagement with an endoscope releasably connecting the handle to an endoscope such that the internal lumen of the device port communicates with an internal lumen of the endoscope. The method includes inserting the distal end of the sheath through the internal lumen of the device port and through the internal lumen of the endoscope, advancing the distal end of the sheath outside of the endoscope at a medical treatment site, and actuating the actuator of the handle to actuate the end effector unit.

In various embodiments, the method may include one or more of the following additional features: wherein the internal lumen of the device port extends along a longitudinal axis substantially parallel to a longitudinal axis of the endoscope; wherein the handle includes a housing for the actuator, the housing and actuator extending along an axis substantially perpendicular to the longitudinal axis of the at least one device port; wherein actuating the actuator includes movement of the actuator along an axis traverse to the longitudinal axis of the internal lumen of the device port; manipulating material with the end effector unit at the treatment site; inserting a second medical device through an internal lumen of a second device port of the handle along a longitudinal axis substantially parallel to the longitudinal axis of the internal lumen of the device port and advancing the second medical device through the internal lumen of the endoscope and to a position outside of the endoscope at a medical treatment site; and wherein the second medical device is a lithotriptor and the method further comprises treating material with the lithotriptor at the treatment site.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 1A illustrates a side partial cross-sectional view of a single operator retrieval device handle in an open position, according to an embodiment of the present invention.

FIG. 1B illustrates the single operator retrieval device of FIG. 1A in a closed position.

FIG. 2A illustrates a side, partial cross-sectional view of a single operator retrieval device handle having a living hinge actuation mechanism in an open position, according to a further embodiment of the present invention.

FIG. 2B illustrates the single operator retrieval device handle having a living hinge actuation mechanism of FIG. 2A in an open position.

FIG. 8 is an alternative view of the handle of FIG. 6.

FIG. 9 illustrates an alternative handle embodiment including an actuation mechanism.

DESCRIPTION OF THE EMBODIMENTS

Figure 1C:
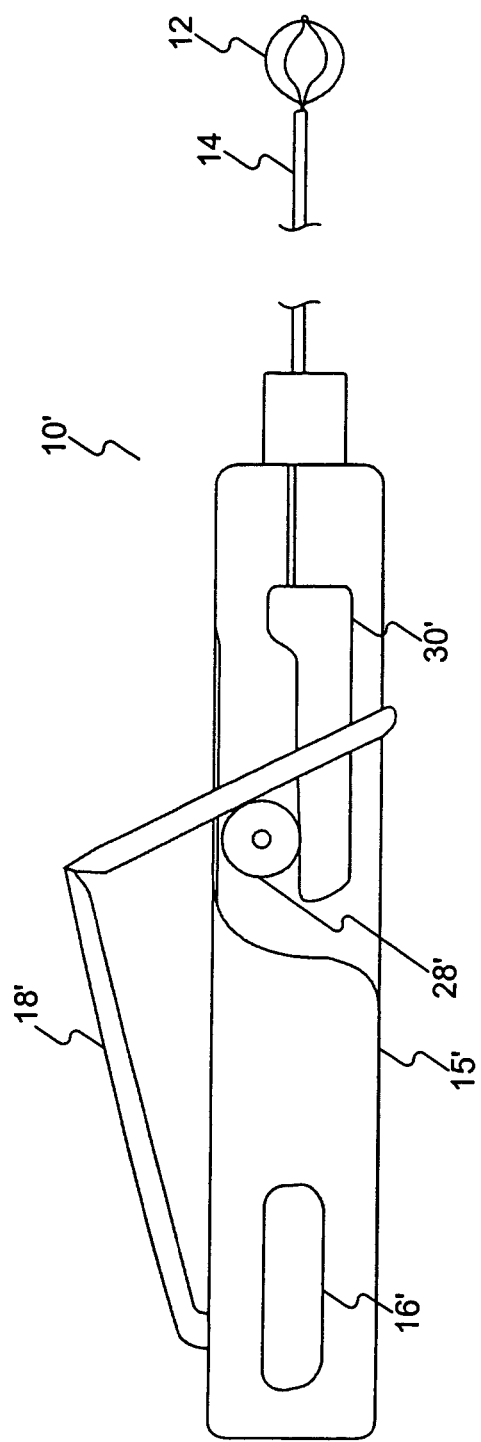
FIG. 1C illustrates an alternative configuration for a single operator retrieval device handle, according to another embodiment of the present invention.

Reference will now be made in detail to the present exemplary embodiments of the invention illustrated in the accompanying drawings. Wherever possible, the same reference numbers will be used throughout the drawings to refer to the same or like parts.

Referring to FIGS. 1A and 1B, one embodiment of a medical device, according to the invention, includes a handle 10, a sheath 14, and an end effector unit 12. Sheath 14 may be flexible and includes an internal lumen for receiving the proximal end of the end effector unit 12. As will be described more in detail below, the end effector unit 12 and sheath 14 are movable relative to each other in order to achieve a first collapsed state of the end effector unit 12 (seen in FIG. 1B) in which the end effector unit 12 is collapsed within the lumen of the distal end of the sheath 14 and a second state in which the end effector unit 12 extends from the distal end of the sheath 14 and expands (seen in FIG. 1A). End effector unit 12 may comprise a basket, grasper, snare, any other retrieval or grasping mechanism, or any other mechanism for performing an operation in a body and may be suitable for urological, endoscopic, or other like procedures. Unit 12 is illustrated as a basket having a plurality of legs.

FIG. 1A illustrates that handle 10 and sheath 14 extend along the same longitudinal axis 20. Handle 10 further includes an elongated handle body 15 housing an actuation mechanism. The end effector unit 12 extends distally from an elongated member disposed within the lumen of sheath 14. The elongated member extends proximally from the end effector unit 12 into the handle body 15 and may be in the form of a flexible shaft, coil, cable, or wire. In one configuration, the proximal end of the elongated member is connected to a movable internal portion of the handle body 15, such that movement of the movable internal portion will move the end effector unit 12 relative to sheath 14 between expanded and collapsed states. This configuration is shown in FIGS. 1A-1B. In another configuration not shown, the proximal end of the sheath 14 may be connected to a movable internal portion of the handle body 15, such that movement of the movable internal portion will extend the sheath 14 over the end effector unit 12 and thereby collapse the end effector unit 12.

Handle 10 is gripped in the palm of an operator and may include a finger ring 16 (also shown in FIGS. 4A-4B) to assist in handling. Handle body 15 further includes an actuating lever 18 attached near a distal end of the handle body 15 by means of a hinge spring 22. The actuating lever 18 extends longitudinally along the handle body 15 and is biased, by hinge spring 22, to a rest position extending at an angle above the handle body 15. The actuating lever 18 bends about an actuating lever pivot 24 and extends proximally internal to the handle body through an opening 27, as represented in FIGS. 1A-1B.

The portion of actuating lever 18 proximal of the actuating lever pivot 24 includes engaging teeth 26 which cooperatively interfit with the teeth of a pinion gear 28 disposed internally within the handle body 15. The interior of handle body 15 includes a drive block 30 which is connected to the proximal end of the elongated member extending from unit 12. The pinion gear 28 engages the drive block 30 in order to impart movement to the drive block 30 upon actuation of the actuating lever 18. Movement of block 30, as described below, actuates unit 12 between the expanded and collapsed states. Upon actuation, the drive block 30 advances and retracts along internal guide rails 32.

An operator actuates the actuating lever 18 by moving the actuating lever 18 about hinge spring 22 in a direction generally normal to the longitudinal axis 20 of the handle 10 and sheath 14. As seen in the example of FIG. 1B, upon actuation, drive block 30 moves the end effector unit 12 proximally toward the collapsed state within sheath 14.

FIG. 1C illustrates an alternative handle configuration 10' having a finger spool 16'. In FIG. 1C actuating lever 18' is attached near a proximal end of the handle body 15' by means of a hinge spring (not shown). The actuating lever 18' extends longitudinally along the handle body 15' and is biased, by the hinge spring, to a rest position extending at an angle above the handle body 15'. In the configuration of FIG. 1C, the drive block 30' and pinion gear 28' are disposed near the distal end of the handle body 15'. Otherwise the embodiment shown in FIG. 1C has a similar construction and operation as the embodiment of FIGS. 1A-1B.

FIGS. 2A-2B illustrate another handle 10" having an actuation mechanism alternative to the configurations of FIGS. 1A-1B and FIG. 1C. In the embodiment of FIGS. 2A-2B, the portion of actuating lever 18" proximal of the actuating lever pivot 24", includes an actuating lever pin 34, which moves within a groove 36 formed in a side of the proximal portion of handle body 15". In this embodiment, handle 10" may include a drive hub 31 which is connected to the proximal end of the elongated member extending from unit 12.

Upon actuation, the proximal or rearward movement of actuating lever pin 34 is resisted by an internal spring 38. The resistance provided by spring 38 provides tactile feedback to the operator for better control of the end effector expansion. FIG. 2A shows the actuating lever 18" at a rest position extending along the longitudinal axis of the handle body 15" and extending above the handle body 15" at an angle. This position corresponds to the extended, expanded position for end effector unit 12. FIG. 2B shows actuation of the actuating lever 18" in a direction generally normal to the longitudinal axis of the handle 10" and sheath 14. As seen in the example of FIG. 2B, upon actuation, drive hub 31 moves the end effector unit 12 proximally toward the retracted, collapsed state within sheath 14.

Figure 3:
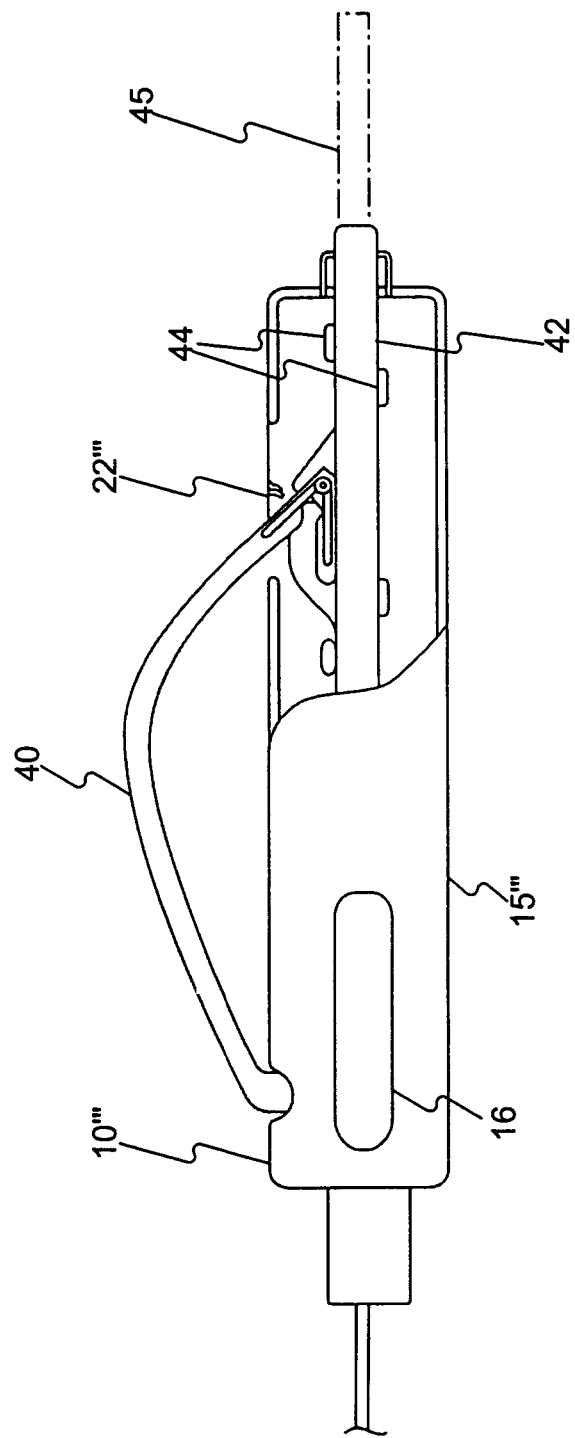
FIG. 3 is a side, partial cross-sectional view of a single operator retrieval device handle having an alternative actuation mechanism, according to a still further embodiment of the present invention.

FIG. 3 illustrates another handle 10'" having an actuation mechanism according to a further embodiment of the present invention. The actuation mechanism includes a bowed actuating lever 40. Bowed actuating lever 40 may be resiliently biased in the bowed state illustrated in FIG. 3. The interior of handle body 15'" in FIG. 3 includes a slide block member 42 attached to the proximal portion of bowed actuating lever 40. Slide block member 42 is connected to the proximal end of the elongated member extending from unit 12 (not shown) similar to drive block 30 of FIGS. 1A-1B.

The slide block 42 is guided through movement by guide bars 44 in the interior of the handle body 15. Because the force imparted to slide block 42 upon actuation of the bowed actuating lever 40 is directed both linearly and longitudinally, guide bars 44 formed on opposing sides of the slide block 42 guide the slide block through longitudinal motion. The slide block member 42 may be attached directly to the bowed actuating lever 40 or connected by a hinge spring 22'". The slide block member 42 may alternatively be attached to the proximal end of sheath 14 for movement between expanded and collapsed states of the end effector unit 12, as explained above. The dashed lines 45 at the proximal end of the handle 15'" of FIG. 3 represent the position of slide block 42 upon actuation of bowed actuating lever 40.

Figure 4A:
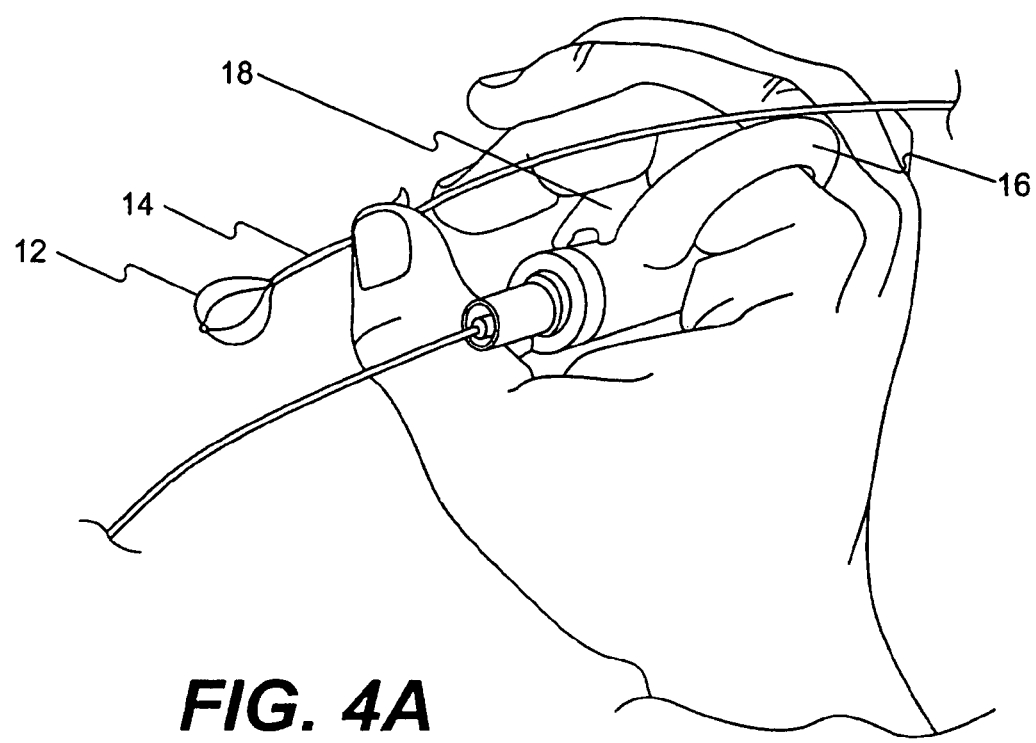
FIG. 4A illustrates an operator positioning a retrieval device according to an embodiment of the present invention in an open position.
Figure 4B:
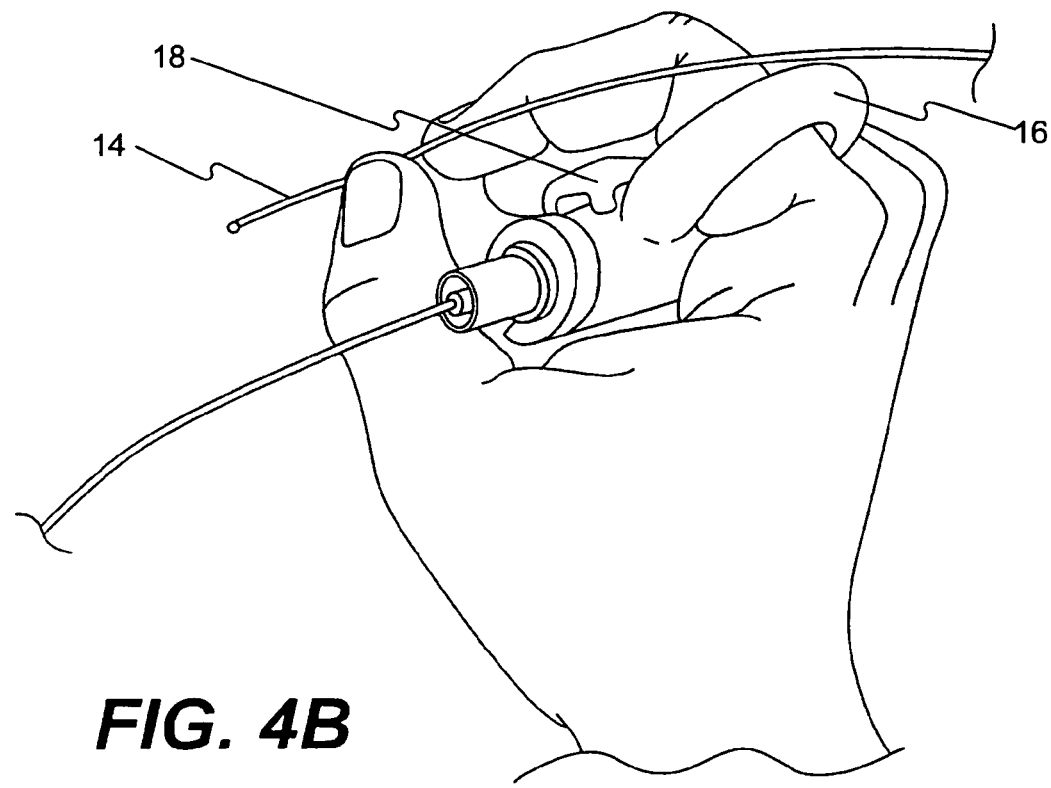
FIG. 4B illustrates an operator positioning a retrieval device according to an embodiment of the present invention in a closed position.

FIGS. 4A-4B illustrate the actuation of any of the previously described handles by an operator. For purposes of the present specification and claims, the term "finger" is intended to include in its scope each of the five digits of the hand, including the thumb. As seen in FIGS. 4A-4B, the operator may insert a finger in finger ring 16 to add stability and control for the operator as the handle is gripped. The finger ring 16 is disposed on an exterior surface of the handle body and positioned approximately 90° relative to the actuation lever 18. This design allows an operator to grip the handle 10 by inserting a finger into the finger ring 16 and leaving the remaining fingers of the handle comfortably positioned for actuation of the actuation lever 18. This design also allows an operator to simultaneously grasp the sheath 14 (as seen in FIGS. 4A-4B) of the device between two or more fingers for forward advancement of the sheath toward a treatment site.

In FIG. 4A, the actuation mechanism is shown in the rest position with the actuating lever 18 disposed under the operator's middle, ring, and end fingers. The operator's index finger and thumb may be used to hold sheath 14 for movement relative to a scope, for example through a scope channel. In FIG. 4B, the actuation mechanism is closed with the actuating lever 18 moved toward a direction essentially normal to the main longitudinal axis of the handle 10 and sheath 14. As represented in FIGS. 4A-4B, the configuration of handle 10 within an operator's grip as well as the direction of actuation allow an operator to grip and advance sheath 14 with the same hand that performs the actuation of unit 12.

Figure 5:
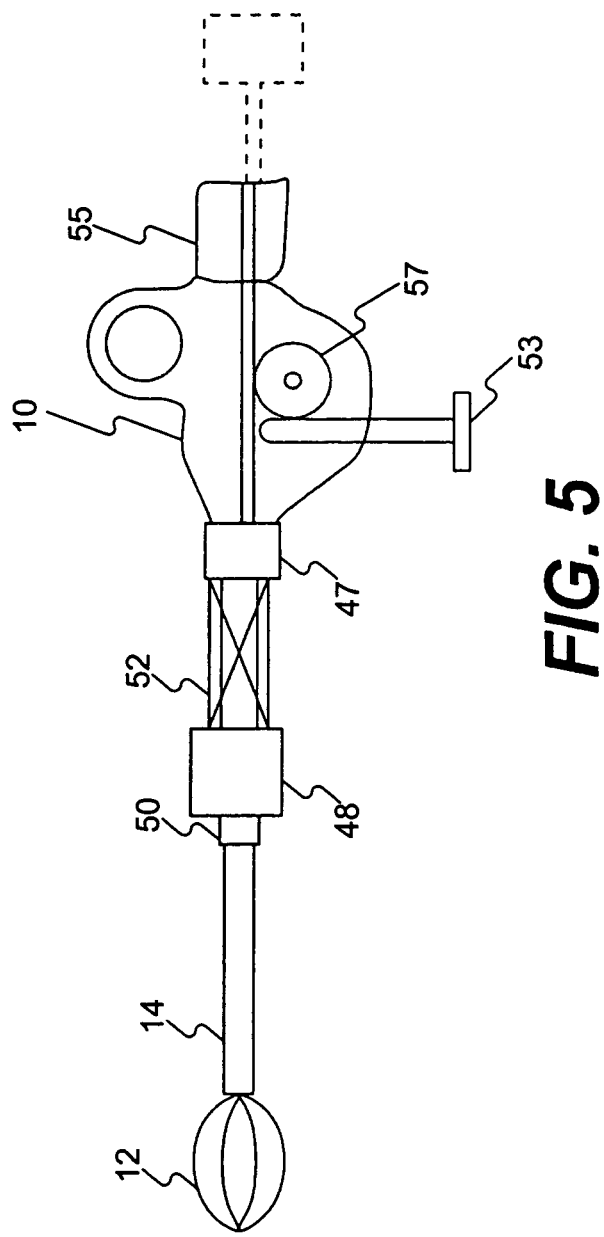
FIG. 5 illustrates an alternative handle, according to another embodiment of the present invention, for connection and movement relative to an endoscope.

FIG. 5 Illustrates a further embodiment of a medical device including a handle 10, a sheath 14, and an end effector unit 12 according to any of the embodiments described above. The medical device of FIG. 5 further includes a proximal adapter hub 47 connected to handle 10, a distal adapter hub 48, and an adapter shaft 50, which receives the sheath 14 and the elongate member. The elongate member is connected to and extends proximally from unit 12. The medical device also includes an adapter spring 52 providing resistance to movement between the handle 10 (connected proximal adapter hub 47) and distal adapter hub 48.

The device of FIG. 5 may access a surgical site through an auxiliary access channel of an endoscope. The distal portion of sheath 14 and end effector unit 12 may be inserted through a medical viewing instrument, such as an ureteroscope for viewing a surgical site during urologic surgery. The sheath and end effector unit 12 may be received within an access channel of an endoscope such that the distal end of the sheath 14 (and end effector unit 12) extends beyond the distal end of the endoscope. Therefore, actuation of the end effector unit 12 can be viewed through the endoscope during a treatment procedure. The distal end of the distal adapter hub 48 may connect to the proximal end of an auxiliary access channel of an endoscope. This connection can take place, for example, by means of a conventional luer fitting formed at the distal end of hub 48.

Upon insertion through an access channel of an endoscope, the medical device of FIG. 5 can be moved relative to the endoscope against the force of adapter spring 52. The sheath 14 may correspond in length to the length of the ureteroscope such that the distal ends of the two devices will be substantially aligned during use. When both medical devices are joined via distal adapter hub 48, sheath 14 and end effector unit 12 can be advanced relative to the distal adapter hub 48, and therefore relative to the ureteroscope. As the sheath 14 and end effector unit 12 are advanced by forward movement of handle 10 with respect to distal adapter hub 48, the adapter spring 52 provides tactile feedback resistance to the operator for better control of relative movement between the devices.

The end effector unit 12 of FIG. 5 is actuated by the use of a finger trigger 53 which engages an internal gear 57 in order to impart motion to a proximal drive 55. Proximal drive 55 can be connected to either the elongated member connected to the end effector unit 12 or to a proximal end of sheath 14. In either case, the actuation of finger trigger 53 imparts motion to the proximal drive 55 thereby actuating the end effector unit 12. The dashed lines at the right hand side of FIG. 5, represent the actuated position of proximal drive 55.

Figure 6:
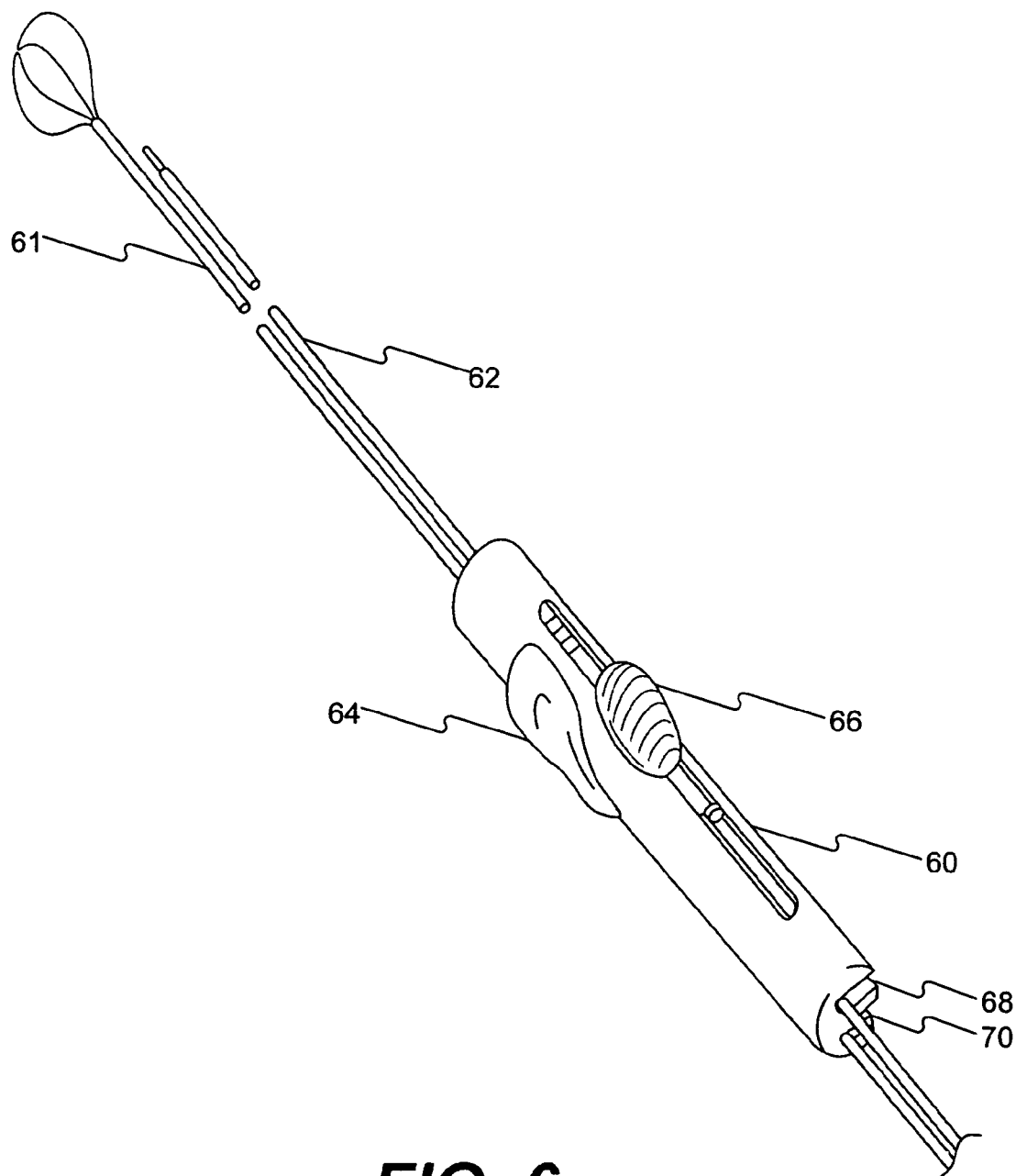
FIG. 6 illustrates a handle for moving multiple medical implements relative to each other during a procedure, according to an embodiment of the present invention.

FIG. 6 illustrates an additional embodiment of the present invention directed to a medical device handle 60 for the relative movement of multiple medical devices. Handle 60, as shown in FIG. 6, houses multiple medical devices, such as a device 61 for manipulating material within a patient's body as described above, in addition to a device for breaking up material, such as a lithotriptor 62. During urological medical procedures, device 61 having an end effector unit for manipulating material will be positioned to grasp material to be removed from a surgical treatment site. Often, material grasped, such as a kidney stone, is too large to be removed from the site without breaking down the material first. A lithotriptor 62, which can include a laser fiber for directing energy and breaking down the subject material, is concurrently introduced with the end effector instrument, which may also be used as a backstop during lithotripsy. Proper alignment and relative movement of the devices is necessary for the safe and efficient breakdown and removal of the unwanted material.

Figure 7:
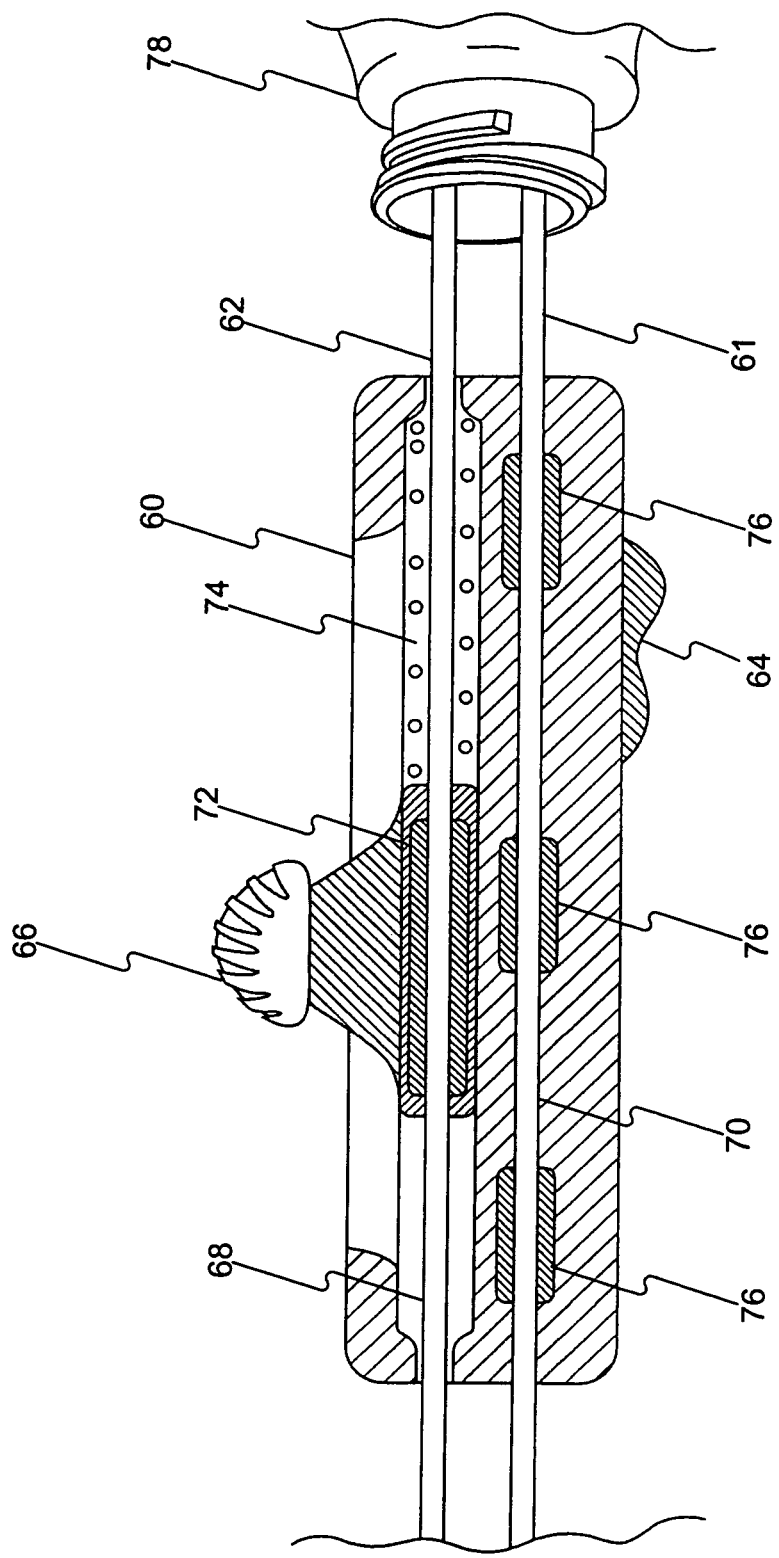
FIG. 7 is a side cross-sectional view of the handle of FIG. 6.

As seen in FIG. 6, medical device handle 60 includes a molded finger grip 64 for enhanced handling, a finger slide 66, and side recess ports 68 and 70. FIG. 7 is a side cross-sectional view of handle 60. Handle 60 may include at least two side recess ports 68 and 70, each configured to receive an elongated medical device shaft therein. As seen in FIG. 8, side recess ports 68 and 70 are externally accessible for enhanced insertion and removal of medical devices therein.

A first recess port 68 may receive a lithotriptor 62 for engagement with a movable internal grip 72. Internal grip 72 may be rubber, polymer, or any other suitable material sized to, for example, receive lithotriptor 62 through a friction fit. Internal grip 72 engages multiple sides of lithotriptor 62 received therein. Internal grip 72 is integrally formed with finger slide 64, which extends to the exterior of the handle 60. Longitudinal movement of the finger slide 64 will move the lithotriptor 62 relative to the device handle 60. FIG. 7 also illustrates a spring 74 disposed in port 68 between the internal grip 72 and a forward end of the handle 60. The resistance provided by spring 72 provides tactile feedback to the operator for enhanced control of longitudinal movement of the device in recess port 68.

A second recess port 70 may receive a device 61 for manipulating material within a patient's body for engagement with at least one stationary internal grip 76. Grip 76 may be rubber, polymer or any other suitable material sized to, for example, receive device 61 through a friction fit. Grip 76 may be manufactured integral with the body of handle 60. As shown in FIG. 7, second recess port 70 may include multiple stationary internal grips 76. Stationary internal grip members 76 prevent any relative longitudinal movement between handle 60 and any medical device received therein. FIG. 7 illustrates that medical devices 61 and 62 may be inserted into an auxiliary access channel of a ureteroscope 78. Accordingly, handle 60 allows for movement of both devices 61 and 62 relative to the viewing area observed by ureteroscope 78. In addition, movement of finger slide 66 allows for relative movement between the devices housed within recess ports 68 and 70.

An alternative handle configuration 80 is illustrated in FIG. 9. Handle configuration 80 is similar to handle 60 of FIGS. 6-8, except that handle 80 includes an actuation mechanism including a trigger 82. As described above with reference to the embodiments of FIGS. 1A-5, handle 80 may include an actuation mechanism for an end effector unit 12 corresponding to a medical device associated with one of the recess ports. Handle 80 allows for relative movement between the medical devices (such as a lithotriptor 62 and a retrieval device 61) as well as actuation of a device (such as unit 12 of retrieval device 61) through the same handle. Any of the handle configurations described above may be substituted and incorporated within the alternative configuration of FIG. 9.

As mentioned above, during some medical procedures, an endoscope is used to provide an operator with access for a medical device (through an internal lumen or working channel of the endoscope) and a view of the internal treatment site. The endoscope is often repositioned to access different treatment sites, to obtain proper placement for performing an operation at a treatment of the site (for example, by providing irrigation through a working channel of the endoscope), or in order to maintain a clear view of a desired treatment site beyond the distal end of the endoscope. In procedures where a retrieval device or a laser fiber is concurrently positioned with an endoscope, the operator must manipulate the endoscope with one hand and position the additional device with the other hand.

Figure 10:
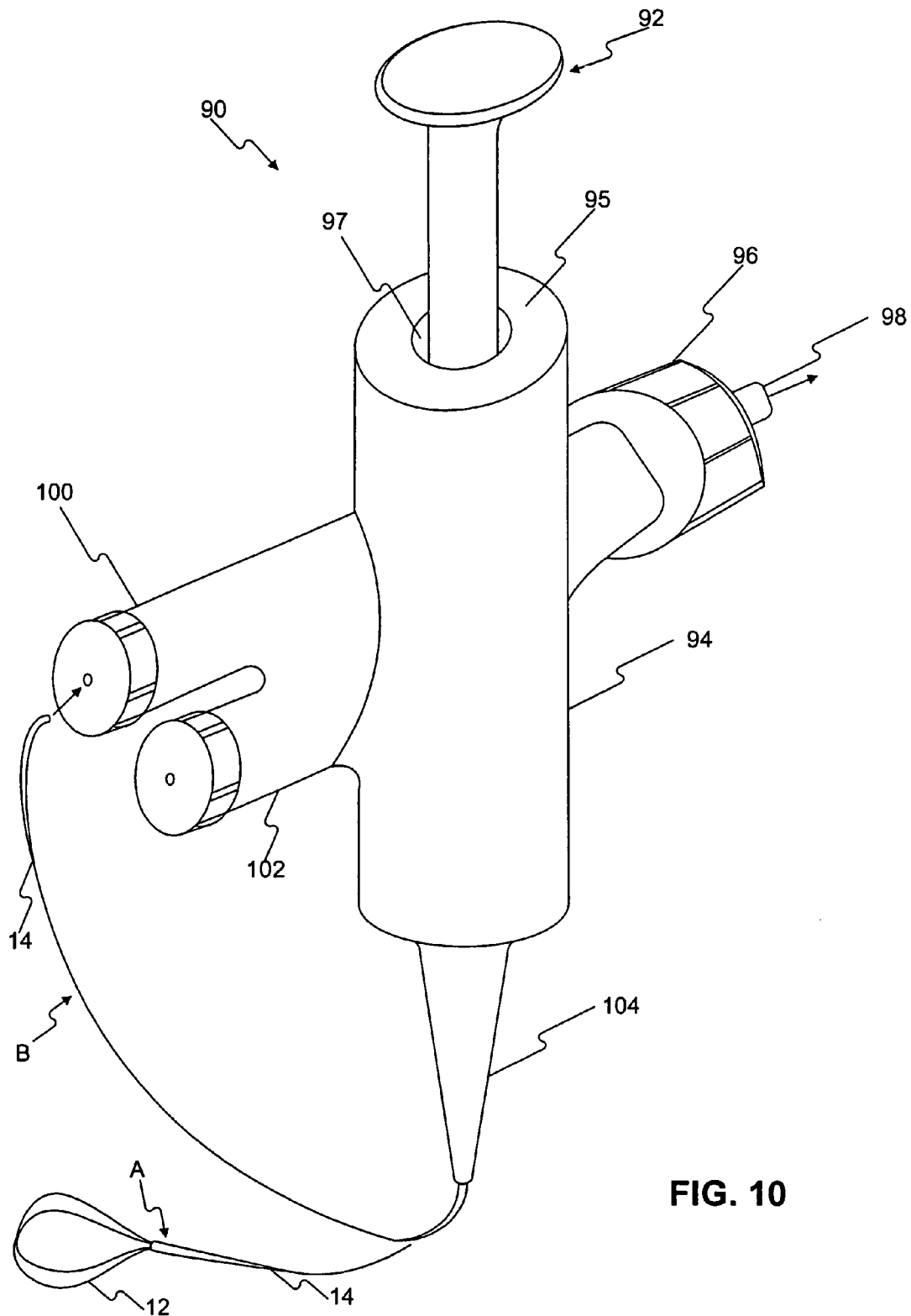
FIG. 10 illustrates an alternative handle, according to another embodiment of the present invention, for connection to an endoscope.
Figure 12:
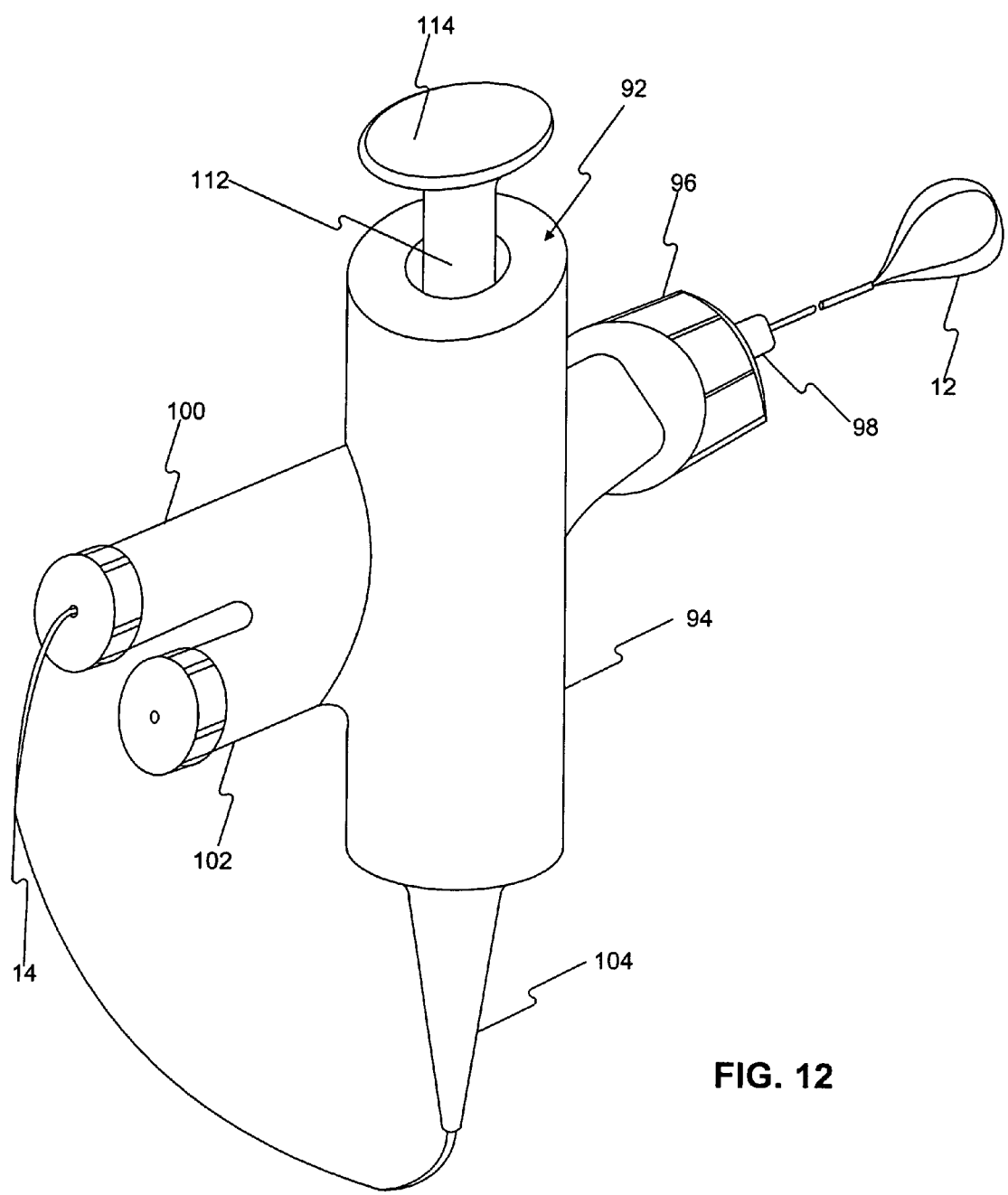
FIG. 12 illustrates the handle of FIG. 10 having an end effector unit in a deployed configuration.

FIG. 10 illustrates an additional embodiment of the present invention directed to a medical device handle 90 adapted for releasable engagement with an endoscope (not shown) for access to an internal lumen of the endoscope. Handle 90 of FIG. 10 includes a medical device including a sheath 14 and an end effector unit 12. As in the embodiments disclosed above, sheath 14 may be flexible and includes an internal lumen for receiving the end effector unit 12. As in the previous embodiments, the end effector unit 12 and sheath 14 are movable relative to each other in order to achieve a first collapsed state of the end effector unit 12 in which the end effector unit 12 is collapsed within the lumen of the distal end of the sheath 14 and a second state in which the end effector unit 12 extends from the distal end of the sheath 14 and expands (seen in FIG. 12). End effector unit 12 may comprise a basket, grasper, snare, any other retrieval or grasping mechanism, or any other mechanism for performing an operation in a body and may be suitable for urological, endoscopic, or other like procedures. End effector unit 12 is illustrated in FIGS. 10 and 12 as a basket having a plurality of legs.

FIG. 10 shows two states of the medical device (sheath 14 and unit 12). The device has a first state (represented by letter "A") in which the device is not inserted into a port of the handle 90. This first state may represent a position of the device when it is packaged and subsequently opened for use. The device has a second state (represented by letter "B") in which the device is inserted into a port of handle 90 and is ready for use.

Similar to the previous embodiments, the end effector unit 12 extends distally from an elongated member disposed within the lumen of sheath 14. The elongated member extends proximally from the end effector unit 12 into the body of handle 90 and may be in the form of a flexible shaft, coil, cable, or wire. In the embodiment illustrated in FIGS. 10-12, the proximal end of the elongated member is connected to a movable internal portion of the handle 90, such that movement of the movable internal portion will move the end effector unit 12 relative to sheath 14 between expanded and collapsed states. Alternatively, the proximal end of the sheath 14 may be connected to a movable internal portion of the handle 90 such that movement of the movable internal portion will extend the sheath 14 over the end effector unit 12 and thereby collapse the end effector unit 12.

Referring to FIG. 10, handle 90 includes an actuator 92, an actuator housing 94, a connector 96 for engagement with an endoscope, a nozzle 98, and first and second device ports 100 and 102 respectively. A strain relief portion 104 is positioned to provide support between the actuator housing 94 and a proximal end of the sheath 14. As seen in FIG. 10, sheath 14 extends from the actuator housing 94 such that the distal end of the sheath 14 can be redirected and inserted along the longitudinal axis of and into the first device port 100. The first device port 100 includes an internal lumen that extends through the body of handle 90 and continues through nozzle 98. The internal lumen of the first device port 100 is adapted to receive the distal end of the sheath 14 and guide the sheath 14 through the lumen to a point where it exits distally from the body of handle 90 at a distal end of nozzle 98. In addition, second device port 102 may include an internal lumen that extends through the body of handle 90 and terminates at the distal end of nozzle 98.

In operation, handle 90 may be releasably operatively engaged with an endoscope in order to enable access with an internal lumen of the endoscope, for example, an auxiliary access channel of an endoscope. The engagement may be achieved by linking connector 96 to the proximal end of an auxiliary access channel (or any internal working lumen of an endoscope) through a threaded engagement, a snap fit connection, a male/female connection, a press fit engagement, or by similar alternative connections. Upon engagement, sheath 14 may access an internal lumen of the endoscope through insertion into the first device port 100 or second device port 102 and beyond the distal end of nozzle 98. Also upon engagement, the first and second device ports 100 and 102 extend along an axis substantially parallel to the longitudinal axis of the endoscope.

The configuration of handle 90 and its actuator 92 permits a single user to operate an endoscope with one hand and activate the medical device in handle 90 with the other hand in a natural, comfortable position of the user's hands and arms. For example, operation of an endoscope is often performed by grasping the proximal end of the scope with one hand such that the longitudinal axis of the scope runs relatively perpendicular to the length of the operator's forearm. Because the device ports 100 and 102 extend along an axis substantially parallel to that of the endoscope, handle 90 can be gripped with the other hand in a manner substantially similar to that used to manipulate the endoscope. In addition, due to the positioning and configuration of both actuator housing 94 and the actuator 92, for example extending substantially perpendicular to the longitudinal axis of the first and second device ports 100 and 102, Actuation of actuator 92 (as described below) is accomplished by a natural movement of the operator's hand. In this configuration, actuation of the actuator 92 is not unlike the movement performed by a musician to depress the valve of a trumpet.

Figures 11A, 11B:
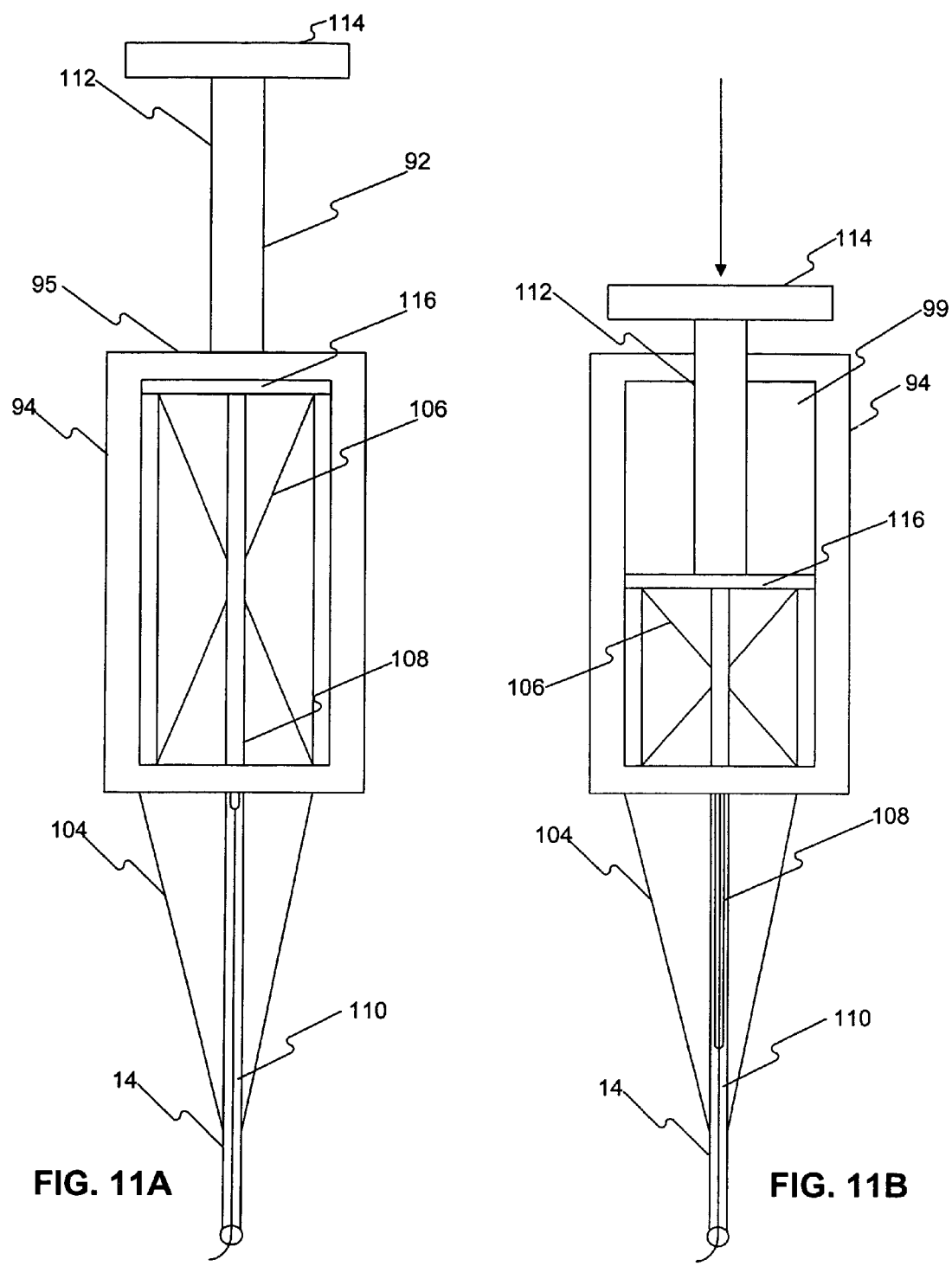
FIG. 11A is a partial side cross-sectional view of the handle of FIG. 10 in a non-actuated position.
FIG. 11B is a partial side cross-sectional view of the handle of FIG. 10 in an actuated position.

FIGS. 11A and 11B illustrate partial side cross-sectional views of the actuation mechanism of handle 90. The actuation mechanism includes an actuator housing 94, an actuator 92, a compression spring 106, and an internal cannula 108. Housing 94 includes a top 95 defining a hole 97. Housing 94 further defines an internal cavity 99 defined by the walls of housing 94. The actuator 92 may include, for example, a plunger 112 having an actuation platform 114 and a base 116. Plunger 112 is received within and movable relative to hole 97. Base 116 may be connected to the internal cannula 108 which receives the proximal end of the elongate member 110. The elongate member 110, in turn, is fastened to the base 116 of plunger 112 such that actuation of the plunger 112 displaces internal cannula 108 and elongated member 110. Sheath 14 is fixedly attached to a distal end of handle 90, for example to strain relief 104.

As seen in FIG. 11A, the compression spring 106 contacts base 116 in order to bias the plunger 112 toward an extended non-actuated position. Upon actuation of the plunger 112 against the biasing force of compression spring 106, base 116, internal cannula 108, and elongated member 110 are all displaced relative to sheath 14, as seen in FIG. 11B. As noted above, because the end effector unit 12 extends distally from the elongated member 110, actuation of plunger 112 will move the end effector unit 12 relative to sheath 14 between collapsed and expanded states. The resistance provided by compression spring 106 provides tactile feedback to the operator for better control of the end effector expansion.

Referring to FIG. 12, actuation of plunger 112 is depicted. During a medical procedure, handle 90 may be operatively engaged with an auxiliary access channel of an endoscope in order to facilitate manipulation of both the endoscope and the end effector unit 12 by an operator. In use, the distal end of sheath 14 can be advanced through and beyond the access channel of an endoscope and positioned relative to the distal end of an endoscope for viewing at a desired treatment site. Once the distal end of sheath 14 is properly positioned at a treatment site within an anatomical lumen of a patient, the same operator of the endoscopic viewing device may deploy the end effector unit 12 as desired upon actuation of the plunger 112.

In addition, a lithotriptor, as described above with reference to FIG. 6, or other desired medical device, may be introduced through the second device port 102 of handle 90 while sheath 14 and unit 12 are used through first device port 100. Accordingly, an operator may control the relative movement between the end effector unit 12 and the distal end of a lithotriptor relative to the viewing area observed by an endoscope at a treatment site. Furthermore, the engagement between handle 90 and the endoscope positions the actuation portions of all three devices (i.e. a retrieval device, a lithotriptor, and an endoscope) in close proximity to a single operator thereby reducing the need for an assistant during medical procedures.

Though shown with a retrieval device (and particularly a basket) and a lithotriptor device, the handles described above can be used with any other medical devices which require actuation or longitudinal positioning of medical devices at a treatment site. The reference to the use of a retrieval device and lithotriptor are used as examples and are not intended to limit the scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for operating a medical device to perform an operation in a body, comprising:
   inserting a medical device into a body, the medical device comprising:
   a sheath including a lumen, a distal end, and a proximal end;
   an end effector unit and an elongate member connected to the end effector unit and extending proximally from the end effector unit within the lumen of the sheath, the end effector unit and sheath movable relative to each other such that in a first state the lumen houses the end effector unit and in a second state the end effector unit extends from the distal end of the sheath;
   a handle including a proximal end and a distal end, the distal end of the handle being connected to the proximal end of the sheath, the handle including an actuator; and
   a ring disposed along an exterior surface of the handle, wherein the ring is located along the handle closer to the distal end of the handle than the proximal end of the handle;
   grasping the handle with a hand of an operator in a position to activate the actuator such that a first finger of the operator's hand is positioned within the ring;
   grasping the sheath with the first finger and another finger of the hand grasping the handle;
   advancing the sheath with the first finger and the another finger of the hand grasping the handle to position the end effector unit near a treatment site; and
   actuating the actuator of the handle with the same hand used to advance the sheath,
   wherein, during the step of actuating the actuator, the ring is stationary relative to a longitudinal axis of the handle, and
   wherein, during the step of actuating the actuator, a longitudinal piece disposed internally within the handle slides relative to a proximal opening in the handle.

2. The method of claim 1, wherein the end effector unit is a basket having a plurality of legs and the basket is collapsed when the end effector unit is in the first state and the basket is expanded when the end effector unit is in the second state.

3. The method of claim 1, wherein grasping the handle includes positioning a second finger of the hand for actuation of the actuator.

4. The method of claim 1, wherein the actuator is an actuating lever that includes a first portion connected to the handle and a second portion formed at an angle to the first portion and wherein actuating the actuating lever comprises locating a first plurality of fingers of the operator at a location positioned to actuate the lever while grasping a distal end of the sheath with a second plurality of fingers from the same hand as the first plurality of fingers.

5. The method of claim 4, wherein grasping the handle with a hand of an operator comprises grasping the handle such that a thumb of the operator is the closest finger of that hand to the proximal end of the sheath.

6. The method of claim 1, wherein the ring is rigid and immovably fixed to the handle.

7. The method of claim 1, wherein the ring projects in a direction orthogonal to the longitudinal axis of the handle.

8. The method of claim 1, wherein the handle includes only one ring.

9. The method of claim 1, wherein the ring is not located on the actuator.

10. A method for operating a medical device to perform an operation in a body, comprising:
    inserting a medical device into a body, the medical device comprising:
    a sheath including a lumen, a distal end, and a proximal end;
    an end effector unit and an elongate member connected to the end effector unit and extending proximally from the end effector unit within the lumen of the sheath, the end effector unit and sheath movable relative to each other such that in a first state the lumen houses the end effector unit and in a second state the end effector unit extends from the distal end of the sheath;
    a handle including a proximal end and a distal end, the distal end of the handle being connected to the proximal end of the sheath, the handle including an actuator; and
    a ring disposed along an exterior surface of the handle, wherein the ring is located along the handle closer to the distal end of the handle than the proximal end of the handle;
    grasping the handle with a hand of an operator in a position to activate the actuator such that a first finger of the operator's hand is positioned within the ring;
    grasping the sheath with the first finger and another finger of the hand grasping the handle;
    advancing the sheath with the first finger and the another finger of the hand grasping the handle to position the end effector unit near a treatment site; and
    actuating the actuator of the handle with the same hand used to advance the sheath,
    wherein, during the step of actuating the actuator, the ring is stationary relative to a longitudinal axis of the handle, and wherein the ring is disposed on an exterior surface of the handle about 90° relative to the actuator, the about 90° being measured on a plane orthogonal to a longitudinal axis of the handle.

11. A medical device, comprising:
    a sheath including a lumen, a distal end, and a proximal end;
    an end effector unit and an elongate member connected to the end effector unit and extending proximally from the end effector unit within the lumen of the sheath, the end effector unit and sheath movable relative to each other such that in a first state the lumen houses the end effector unit and in a second state the end effector unit extends from the distal end of the sheath;
    a handle connected to the proximal end of the sheath and a proximal end of the elongate member, the handle comprising an actuator including a first portion disposed proximate a distal end of the handle and a second portion formed at an angle to the first portion, the second portion extending into the handle through an opening in the handle:
    wherein the handle is configured to allow a single hand of an operator to attain a single position to actuate the end effector unit via the actuator and grasp and manipulate the distal end of the sheath; and
    a ring disposed on an exterior surface of the handle, the ring configured to accommodate a first finger of the single hand, wherein the ring is located along the handle closer to the distal end of the handle than a proximal end of the handle, wherein the handle includes only one ring, wherein the ring and the first portion of the actuator are located at the same axial position along the handle, and wherein the ring is stationary relative to a longitudinal axis of the handle as the actuator is actuated, wherein the actuator is operatively connected to a longitudinal piece disposed internally within the handle, the longitudinal piece being slidable relative to a proximal opening in the handle when the actuator is actuated, and wherein the ring is disposed along an exterior surface of the handle about 90° relative to the actuator, the about 90° being measured on a plane orthogonal to a longitudinal axis of the handle.

12. The medical device of claim 11, wherein the actuator is an actuator lever.

13. The medical device of claim 11, wherein the ring is positioned to permit a second finger of the single hand to actuate the actuator when the first finger is within the ring.

14. The medical device of claim 13, wherein the ring is positioned to permit at least a third finger of the single handle to grasp and manipulate the sheath when the first finger is within the ring and the second finger is positioned to actuate the actuator.

15. The medical device of claim 11, wherein the ring is immovably fixed to the handle.

16. The medical device of claim 11, wherein the ring projects in a direction orthogonal to the longitudinal axis of the handle.

17. The medical device of claim 11, wherein the ring is not located on the actuator.

* * * * *

UNITED STATES PATENT AND TRADEMARK OFFICE
CERTIFICATE OF CORRECTION

| | | |
|---|---|---|
| PATENT NO. | : 8,512,350 B2 | Page 1 of 1 |
| APPLICATION NO. | : 10/999914 | |
| DATED | : August 20, 2013 | |
| INVENTOR(S) | : Tim E. Ward | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1162 days.

Signed and Sealed this

Thirteenth Day of January, 2015

Michelle K. Lee
*Deputy Director of the United States Patent and Trademark Office*